(12) United States Patent
Rosen et al.

(10) Patent No.: US 11,071,799 B2
(45) Date of Patent: Jul. 27, 2021

(54) PORTABLE AND DISPOSABLE UV DEVICE

(71) Applicant: Freestyle Partners, LLC, Chicago, IL (US)

(72) Inventors: Jennifer K. Rosen, Chicago, IL (US); Benjamin X. Feeney, Chicago, IL (US); Gregory D. DeGrazia, Birmingham, MI (US)

(73) Assignee: Freestyle Partners, LLC, Detroit, MI (US)

( * ) Notice: Subject to any disclaimer, the term of this patent is extended or adjusted under 35 U.S.C. 154(b) by 0 days.

(21) Appl. No.: 16/809,976

(22) Filed: Mar. 5, 2020

(65) Prior Publication Data

US 2020/0215214 A1 Jul. 9, 2020

Related U.S. Application Data

(63) Continuation-in-part of application No. 16/279,253, filed on Feb. 19, 2019.

(Continued)

(51) Int. Cl.
*A61L 2/10* (2006.01)
*A61L 2/08* (2006.01)
(Continued)

(52) U.S. Cl.
CPC ............... *A61L 2/10* (2013.01); *A61L 2/084* (2013.01); *A61L 2/24* (2013.01); *A61L 9/20* (2013.01);
(Continued)

(58) Field of Classification Search
CPC ...... A61L 2/0047; A61L 2/0052; A61L 2/084; A61L 2/10; A61L 2/24; A61L 9/20;
(Continued)

(56) References Cited

U.S. PATENT DOCUMENTS 2,215,635 A * 9/1940 Collins ..................... A61L 2/10
250/494.1
2,720,145 A * 10/1955 Goodfellow ......... G03B 17/565
396/74

(Continued)

FOREIGN PATENT DOCUMENTS

WO 2016196904 A1 12/2016

OTHER PUBLICATIONS

Buonanno et al. "Germicidal Efficacy and Mammalian Skin Safety of 222-nm UV light"; Radiation Research 187, 493-501 (2017) (Year: 2017).*

(Continued)

*Primary Examiner* — Timothy C Cleveland
(74) *Attorney, Agent, or Firm* — Gregory D. DeGrazia; Miller, Canfield, Paddock & Stone PLC (57) ABSTRACT

A handheld portable device for sanitizing a surface or air surrounding a surface. The handheld portable device includes a body that comprises a user input and a UVC light source disposed at the body. The handheld portable device also includes a power source for providing power to the UVC light source. Responsive to actuating the user input, such as by a user holding the handheld portable device, the UVC light source emits UVC light to sanitize the surface or the air surrounding the surface of pathogens. The handheld portable device includes a visible light emitter that, when powered, emits visible light to indicate the surface or space that is irradiated by the UVC light.

20 Claims, 3 Drawing Sheets

Related U.S. Application Data (60) Provisional application No. 62/963,682, filed on Jan. 21, 2020, provisional application No. 62/694,482, filed on Jul. 6, 2018, provisional application No. 62/632,716, filed on Feb. 20, 2018.

(51) Int. Cl.
*A61L 2/24* (2006.01)
*A61L 9/20* (2006.01)

(52) U.S. Cl.
CPC ........ *A61L 2202/11* (2013.01); *A61L 2202/16* (2013.01); *A61L 2209/12* (2013.01)

(58) Field of Classification Search
CPC ............. A61L 2202/11; A61L 2202/14; A61L 2202/16; A61L 2209/12
See application file for complete search history.

(56) References Cited

U.S. PATENT DOCUMENTS

| | | | |
|---|---|---|---|
| 6,201,933 B1* | 3/2001 | Hylen | G03B 1/48 396/316 |
| 6,650,085 B2 | 11/2003 | Lau et al. | |
| 8,105,532 B2 | 1/2012 | Harmon et al. | |
| 8,357,914 B1 | 1/2013 | Caldwell | |
| 8,753,575 B2 | 6/2014 | Neister | |
| 8,847,174 B2 | 9/2014 | Domenig et al. | |
| 9,572,903 B2 | 2/2017 | Dobrinsky et al. | |
| 9,649,398 B1 | 5/2017 | York | |
| 9,700,642 B2 | 7/2017 | Neister | |
| 9,767,337 B2* | 9/2017 | Furlong | G06K 7/1413 |
| 2006/0188389 A1 | 8/2006 | Levy | |
| 2008/0295271 A1 | 12/2008 | Perunicic | |
| 2008/0310996 A1 | 12/2008 | Kim et al. | |
| 2011/0256019 A1 | 10/2011 | Gruen et al. | |
| 2016/0106873 A1 | 4/2016 | Dobrinsky et al. | |
| 2017/0080251 A1 | 3/2017 | Yehezkel | |
| 2017/0157276 A1 | 6/2017 | Dobrinsky et al. | |
| 2017/0216466 A1 | 8/2017 | Dujowich et al. | |
| 2017/0225206 A1 | 8/2017 | Deitchman et al. | |
| 2017/0245616 A1 | 8/2017 | Lakios et al. | |
| 2018/0236113 A1* | 8/2018 | Gross | A61L 2/10 |
| 2019/0255201 A1 | 8/2019 | Rosen et al. | |

OTHER PUBLICATIONS

Narita et al., Chronic irradiation with 22-nm UVC light induces neither DNA damage nor epidermal lesions in mouse skin, even at high doses; PLoS One. 2018; 13(7) (2018) (Year: 2018).*

Nerandzic et al., "Evaluation of a hand-held far-ultraviolet radiation device for decontamination of Clostridium difficile and other healthcare-associated pathogens" U.S. National Library of Medicine, National Institutes of Health, BMC Infect. Dis. May 16, 2012.

Coxworth, "Human-safe ultraviolet light used to kill airborne viruses" New Atlas article, Feb. 9, 2018, https://newatlas.com/far-uvc-airborne-viruses/53349/.

Welch et al., "Far-UVA light: A new tool to control the spread of airborne-mediated microbial diseases" Scientific Reports 8, Article No. 2752, Feb. 9, 2018, https://www.nature.com/articles/s41598-018-21058-w.

Lapook, "How ultraviolet light could be used to tight the flu" CBS news, Feb. 12, 2018, https://www.cbsnews.com/news/how-ultraviolet-light-could-be-used-to-fight-the-flu/.

International Search Report and Written Opinion dated Jun. 20, 2019 for corresponding PCT Application No. PCT/US2019/018517.

* cited by examiner

PORTABLE AND DISPOSABLE UV DEVICE

CROSS REFERENCE TO RELATED APPLICATIONS

The present application claims priority of U.S. provisional application Ser. No. 62/963,682, filed Jan. 21, 2020, which is hereby incorporated herein by reference in its entirety. The present application is also a continuation-in-part of U.S. patent application Ser. No. 16/279,253, filed Feb. 19, 2019, which claims the filing benefits of U.S. provisional application Ser. No. 62/694,482, filed Jul. 6, 2018, and U.S. provisional application Ser. No. 62/632,716, filed Feb. 20, 2018, which are all hereby incorporated herein by reference in their entireties.

FIELD OF THE INVENTION

The present invention relates generally to light-emitting apparatus and, more particularly, to a far short-wavelength ultraviolet light emitting device.

BACKGROUND OF THE INVENTION

Pathogens such as bacteria and viruses are everywhere, such as on door handles, on phones, on television remotes, in public bathrooms, on counter tops, on the sidewalks, airborne, etc. Currently, there exists many solutions to cleaning hands from germs, such as hand sanitizer, wet wipes, etc. These products may help people who are on the go or who want a quick solution to cleaning their hands when washing with soap is not an option. However, pathogens are everywhere and it is often not feasible to put chemical wipes and/or cleaning solutions on all surfaces and/or in the air that are desired to be disinfected.

Aside from chemical wipes and other cleaning solutions, short-wavelength ultraviolet (UVC) light is a proven and effective way to kill bacteria and other pathogens. Current UVC options for killing germs/bacteria, such as portable UVC wands, stationary mechanisms to step on that help clean bottoms of shoes, phone cases, etc., are often expensive and are not readily accessible to the average consumer and/or often have a singular specific use (e.g., only cleaning the person's shoes or other element or device). Furthermore, there are risks with UVC light. For example, UVC light may cause skin cancer and/or cataracts. Therefore, a need exists for a safe for humans, handheld and/or portable and/or disposable and/or rechargeable device that may be used to sanitize selected surfaces, localized areas, and/or air surrounding such surfaces to eliminate pathogens in a format that is readily available and accessible for everyday use for the average consumer.

SUMMARY OF THE INVENTION

UVC light provides an effect of killing pathogens. The present invention provides ultraviolet (UV) or UVC light (e.g., far-UVC or short-wave UV light) in a handheld and/or portable and/or disposable and/or rechargeable format that may be utilized in everyday, common place settings to sanitize selected surfaces, localized areas, and/or air surrounding a surface that is safe for humans while eliminating pathogens. The device may be readily available and accessible for everyday use for the average consumer.

Another aspect of the disclosure provides a handheld UVC device for generating and emitting UVC light on selected surfaces, localized areas and air surrounding a surface. The device includes an irradiation portion or light source that provides irradiation or light in the UVC spectrum for generating and emitting UVC light toward a surface or space surrounding a surface. The device also includes an activation portion. The activation portion provides selective activation of the irradiation portion for a time duration sufficient to episodically generate and emit UVC light to sanitize the surface or space. The device also includes a grip. The grip provides a gripping surface for a user to grip the device and direct the irradiation portion toward the surface or space to be sanitized and to emit UVC light toward the surface or space to be sanitized.

The device may be modular. That is, different components of the device (e.g., a handle, the irradiation portion, a lens) may be detachably attached to the device and/or disposable. The device may include a visible light emitter that emits at least one indicia or shape (e.g., a circle or a square or other polygon) that indicates a surface or object that is irradiated by the UVC light. The at least one indicia or shape may include a plurality of concentric shapes (e.g., a plurality of concentric circles or polygons). The device may include one or more lens and the UVC light may pass through the lenses to focus or disperse the UVC light.

Another aspect of the disclosure provides a method of sanitizing a surface. The method includes providing a handheld device that includes a first light source that emits UVC light and a second light source that emits visible light. The method also includes emitting, by the first light source of the handheld device, UVC light. The method also includes emitting, by the second source of the handheld device, visible light. The visible light provides visible indication as to the aim direction of the emitted UVC light. The method also includes aiming the emitted UVC light toward the surface to be sanitized by directing the emitted visible light at the surface to be sanitized and indicating, by the handheld device, when the handheld device is an optimal distance from a surface to be sanitized. In response to the indication that the device is an optimal distance from the surface to be sanitized, the method includes sanitizing the surface by irradiating the surface with the emitted UVC light. Indicating when the handheld device is an optimal distance may include focusing the emitted visible light at the surface when the handheld device is an optimal distance from the surface to be sanitized.

These and other objects, advantages, purposes and features of the present invention will become apparent upon review of the following specification in conjunction with the drawings.

DESCRIPTION OF THE PREFERRED EMBODIMENTS

A handheld and/or portable and/or disposable and/or rechargeable device for sanitizing a surface or air surrounding the surface operates to emit ultraviolet (UV) or UVC light (e.g., far-UVC light) in order to eliminate pathogens. The device includes a unit with an activation mechanism. When the activation mechanism is activated, the device emits UVC light. The device may then be manipulated so that the desired surface and/or air and/or space to be sanitized is irradiated in the UVC light, thereby cleansing the surface and/or air of pathogens.

Figure 1:
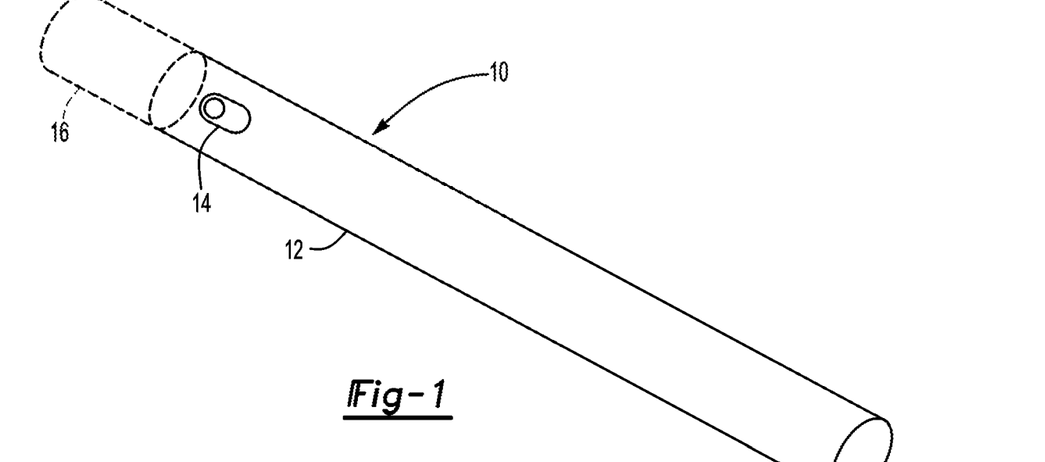
FIG. 1 is a perspective view of portable device that emits UVC light when activated in accordance with the present invention.

Referring now to the drawing and the illustrative embodiment depicted therein, a device 10 includes a unit 12. The unit 12 may be any suitable shape and at least a portion of the unit 12 is transparent or translucent. The unit 12 includes an activation mechanism 14. While the illustrated embodiment shows the activation mechanism as a switch or toggle, it is understood that the activation mechanism may take any number of forms, which are described in more detail below. When the activation mechanism 14 is activated, the unit 12 emits UVC light through the transparent or translucent portion. Optionally, the unit includes a power source 16.

Pathogens such as bacteria and viruses are everywhere, such as on door handles, on phones, on television remotes, in public bathrooms, on counter tops, on the sidewalks, airborne, etc. Currently, there exists easy and affordable solutions to cleaning hands from germs such as Purell hand sanitizer, Wet Wipes, etc. These products help people who are on the go or who want a quick solution to cleaning their hands if washing with soap is not an option. However, pathogens are everywhere and it is often not feasible to put chemical wipes and/or cleaning solutions on all surfaces and/or in the air that are desired to be disinfected.

Aside from chemical wipes and other cleaning solutions, short-wavelength ultraviolet (UVC) light is a proven and effective way to kill bacteria and other pathogens. While currently some UVC options for killing germs/bacteria exist, such as portable UVC wands, stationary mechanisms to step on that help clean bottoms of shoes, phone cases, etc., these UVC light options are often expensive and not readily accessible to the average consumer and often have a singular specific use (e.g., only cleaning the person's shoes or other element or device). Also, there are risks with UVC light (for example, it may cause skin cancer and/or cataracts). Electromagnetic (EM) radiation includes all light or illumination or irradiation that propagates electromagnetic radiant energy through space using waves. EM radiation, for example, includes both visible (to the human eye) radiation and invisible radiation, such as visible light, radio waves, microwaves, ultraviolet, gamma rays, etc. UVC light or illumination or irradiation is shortwave germicidal ultraviolet EM radiation that is generally 100 nm to 280 nm in wavelength. However, far-UVC light or illumination or irradiation, which is a narrow spectrum within UV light (e.g., 200 nm to 230 nm), may provide the same effect of killing germs/bacteria without the harming side effects. As used herein, light and illumination and irradiation may be used interchangeably to refer to either visible or invisible EM radiation.

In accordance with the present invention, a device to reduce germs and increase health by putting the sterilizing power of UV or UVC light in an inexpensive, disposable and/or single-use (or few uses), and portable format for everyday use is provided. The device comprises a small portable unit (that may take any number of shapes) that, when activated, emits UVC light. In some examples, the device may emit other types of UV light (emitting light within other spectral bands or having different wavelengths) that also eliminates bacteria and/or other pathogens. The unit may be activated by any number of means, such as actuating a switch or bending, pressing, squeezing, shaking and/or exposing the unit to air to activate it. After activation, the UVC light may be used to irradiate surfaces to kill pathogens and remains activated for a limited duration (similar to, for example, a typical chemical glow stick or chemical hand warmer). The device may sanitize many types of surfaces (e.g., an epidermis or a non-biological surface such as a table). The device may also irradiate the air to cleanse and kill pathogens above and/or around the surfaces. The device may then be easily disposed of (for example, in a trash can) once the UVC light terminates. The present invention is more effective and has more applications than traditional chemical wipes or cleaning solutions, is not harmful like traditional UVC light, is easy to activate, and allows for portability.

The device may utilize a variety of means to generate power to power or energize a UVC light source (disposed in the body or unit). For example, the device may use disposable or rechargeable batteries, chemicals, solar power, wind power, and/or any other type of mechanism to activate and/or generate the UVC light. Optionally, the UVC light source may emit light responsive to a chemical reaction when the device or unit is bent, squeezed, shaken or the like. Alternatively, the device may activate or deactivate through the actuation of a switch, button, etc.

In another aspect of the invention, the device may use a rechargeable battery to allow for multiple uses of the device (where the device may be plugged in to recharge). In yet another aspect of the invention, the device may comprise any suitable form of mobile device, such as, for example, a cell phone or other mobile device that is operable to toggle between emitting no light, regular visible light (such as a flashlight function), and UVC light. The device, in some examples, may include a traditional flashlight form. That is, the device may be a flashlight with a reusable UV light source (a light emitting diode (LED), fluorescent bulb, excimer lamp, etc.) and a power source (replaceable batteries, rechargeable batteries, non-replaceable batteries, capacitors, etc.).

The device may emit UVC light (or other pathogen-cleansing UV light) in any number of ways. This includes using light sources of various technologies (incandescent, fluorescent, LED, excimer lamp, etc.). When including a light source, the light source may take any appropriate shape. For example, the light source and/or reflector may be shaped to focus the emitted light into a relatively narrow area. The user, in some examples, may focus the emitted light (e.g., by moving a lens of the device or by actuating some other user input) between generally broad beams and generally narrow beams. The device may emit a visible indication as to the aim direction of the emitted UVC light. For example, the device may emit visible crosshairs (i.e., visible light in the shape of crosshairs) or other targeting indicia to assist in directing or aiming the invisible (to the human eye) UVC light. That is, the device may provide a method to "aim" the UVC light so that the intended areas are cleansed.

The device may also emit visible light focused generally in the same area as the UVC light to assist the user in directing or aiming or guiding the UVC light (i.e., the user illuminates the area to be cleansed with the visible light). For example, the device may emit a beam of visible light such as a typical flashlight does, and wherever the emitted visible light irradiates a surface or space, the emitted UVC light also irradiates (invisibly, to the human eye) that surface or space. The visible light emitter (that emits the crosshairs) may be powered via actuation of a user input, such as the same user input that activates the UVC emitting light source, such that the visible light emitter and the UVC light emitter are operated in tandem, whereby the emitted visible light is visible at the area where the UVC light is directed. Optionally, the device may include a second user input, separate from the user input that activates the UVC emitting light source, such that the visible light emitter is operated independently of the UVC emitting light source. In another example, the light source may be a lamp that emits UVC light in a generally 360 degree area around the light source (e.g., a cylinder-shaped bulb or diode or the like). The device may then emit light in all or nearly all directions to cleanse a large area simultaneously. In some examples, the light source or light emitting diode or light bulb is replaceable and/or disposable.

In some implementations, the device may include a timer. The timer may begin measuring time when the user input to power the UVC light emitting light source is actuated. The timer may measure a period of time that is sufficient for the UVC light to eliminate a majority of pathogens (e.g., ten seconds). The timer may include a visual, audible, or tactile indication that the period of time has elapsed (e.g., an LED, an audio signal, vibration, etc.). Optionally, the timer may disable the light source at the end of the period of time. The timer may be user configurable or allow for selection among a set of predetermined time periods (e.g., ten, thirty, and sixty seconds). Thus, a user may actuate the device via a push of a button and then the device will operate for the predetermined period of time (without further input or holding of the button by the user) and then automatically shut off.

The device may include a lamps that emits UVC light that is generally between 180 nm and 300 nm in wavelength. For example, the lamp may emit light between 200 nm and 235 nm in wavelength. The UVC light in this spectrum is believed to kill pathogens. The device may include a filter (e.g., chemical filtration, an optical filter(s), etc.) to filter UVC light to a narrower spectrum of wavelengths (e.g., to 200 nm to 235 nm). When the light source emits a narrow spectrum of light (e.g., 200 nm to 235 nm), the filter may act as a secondary safety measure to ensure only proper wavelengths are emitted from the device. The light source may also emit a wide range of frequencies and the filter may act as the primary method of controlling wavelength. In some examples, the device may filter UVC light having wavelengths greater than 230 nm. The filter, in some implementations, has a maximum frequency response between 220 nm and 225 nm (e.g., 222 nm). UVC light with a wavelength of approximately 222 nm is still capable of destroying pathogens or otherwise providing antiseptic solutions without causing harm to the epidermis or eyesight of persons exposed to the light. Therefore, it is desirable to avoid light exceeding about 222 nm by a substantial amount (e.g., above 230 nm) with significant intensity. Maintaining irradiation at approximately 222 nm, (e.g., far-UVC irradiation) will destroy pathogens, but may not penetrate epidermis of a human nor penetrate a cornea of a human eye even at high intensities over long periods of time. Chemical filtration may be included in a bulb of the device or a filter located elsewhere within the device. An optical filter may be placed such that light emitted from the device passes through the optical filter. An optical filter may be included in the lamp of the device itself or as a separate element (e.g., as a film on a lens or light source or bulb of the device or between the lens and the lamp). In some examples, the lamp 28 may only generate UVC light that is at or below around 222 nm so that filtration is not required.

Although not necessary, the device 20 may optionally include an eye detection sensor. The eye detection sensor is operable to detect presence of an eye (e.g., a human eye) within a field of sensing of the device. A processor or controller of the device may receive and process sensor data captured by the eye detection sensor (such as a camera that captures image data representative of the scene at or partially around the device and in the path of the UV light emitted by the device) to determine presence of an eye within the field of sensing of the eye detection sensor. The field of sensing of the eye detection sensor may be generally aligned with the light emitted by the device 20. That is, the field of sensing may encompass the area irradiated by the UV light emitted by the device 20. The controller may automatically deactivate or disable the UV light source when an eye is detected within the field of sensing of the eye detection sensor. Optionally, the controller may also or otherwise notify or alert the user to the presence of an eye (e.g., a visual or audible notification such as a buzzer or flashing light).

In accordance with another aspect of the invention, the device emits light that makes bacteria and other pathogens visible to a user of the device to allow the user to determine the cleanliness of an area. For example, the device may emit a fluorescent light that illuminates bacteria. The device may emit the pathogen-illuminating light simultaneously with the UV or UVC light or separately from the UV or UVC light. That is, pathogens may be illuminated (i.e., made visible to the user) as the UVC light is in use to direct the locations to clean or, alternatively, before and after the UVC light is used to assist in cleaning and to assess effectiveness. The pathogen-illuminating light may be emitted from the same light source (e.g., LED or bulb) as the UVC light or from a separate light source (i.e., a pathogen-illuminating light source that emits pathogen-illuminating light). The device may include an additional user input (e.g., button or switch) to activate the pathogen-illuminating light separately from the UVC light.

Figure 2A:
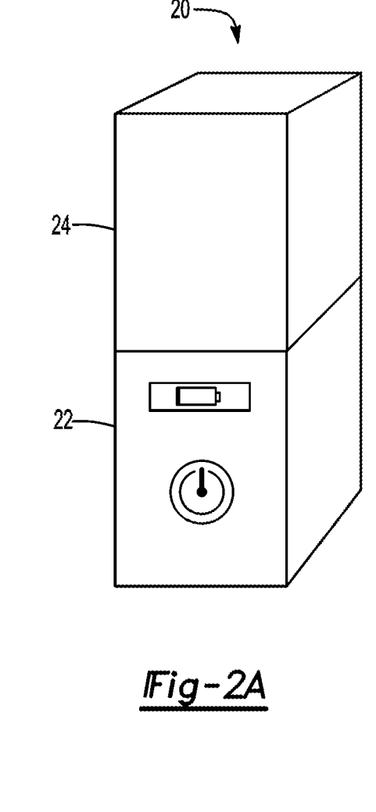
FIGS. 2A and 2B are perspective views of another portable device that emits UVC light when activated in accordance with the present invention.
Figure 2B:
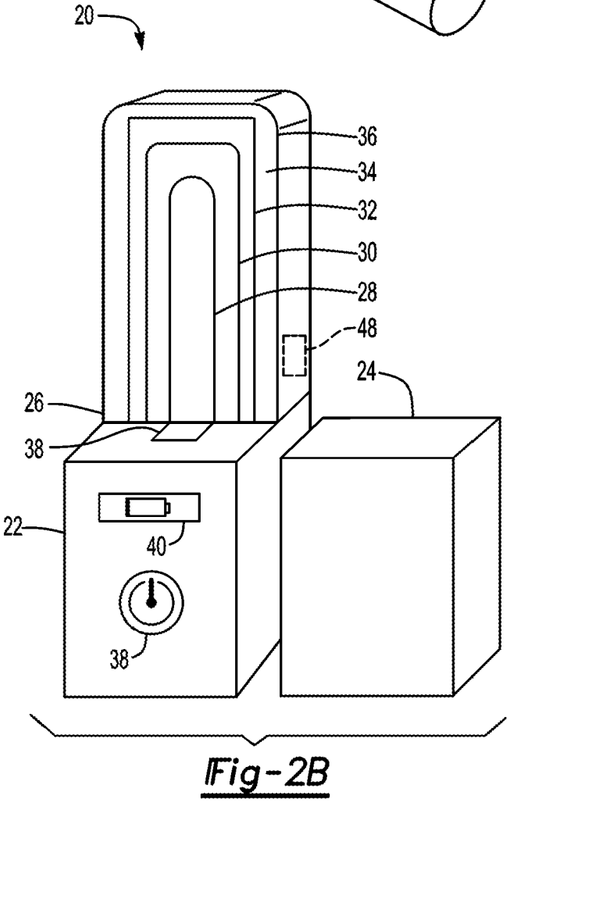

Referring now to FIGS. 2A and 2B, a UVC light emitting device 20 includes a base 22 and a top 24. The base 22 and top 24, while exemplified as a "lipstick case" box shape, may take any suitable form (e.g., rectangular, tubular, triangular, flexible/bendable/conformable, etc.). The top 24 attaches to the base 22 to enclose the device 20 (FIG. 2A). When the top 24 is removed (e.g., by pulling, twisting, releasing a latch, etc.), the radiation or illumination source or lamp housing 26 is exposed. Illumination, as defined herein, refers to illuminating an object or the air with visible or invisible (to a user) light. The lamp housing may include a lamp 28 or other illumination or radiation source or light source that emits UV or UVC light. The lamp 26 may be any lamp that is capable of producing wavelengths in the UVC spectrum (e.g., an excimer or excilamp, LED, etc.). The lamp housing 26 may also house a filter 30 that filters the wavelength of light emitted by the lamp 28. The filter 30 may be activated whenever the illumination or radiation source 28 is activated (e.g., by pushing, pressing, pulling, bending, shaking, etc. the device 20). Optionally, the filter may be replaceable and/or disposable (e.g., a removable filter cartridge 42). The device may also be activated via biometrics (e.g., fingerprint sensor or face identification).

The device may also include a lens 32. The lens 32 may focus the emitted light into a narrower or broader beam. The lamp housing 26 may further include backing 34 and reflective panel 36 to further direct and control the emitted light. In some implementations, the device 20 includes an activation and/or deactivation user input 38 (e.g., a switch, slider, toggle, button, etc.). The user input 38, when actuated or activated, may power or depower the lamp 26, thereby causing the device 20 to emit UVC light or to stop emitting UVC light. The user input may episodically power the lamp 26 for a time duration sufficient to generate and emit UVC light to sanitize the targeted surface or space. The device 20 may further include a power level 40 that indicates the amount of power remaining in a power supply. The power supply may be a replaceable battery, a rechargeable battery, an electrical plug-in supply, a solar powered supply, etc.

Figure 3:
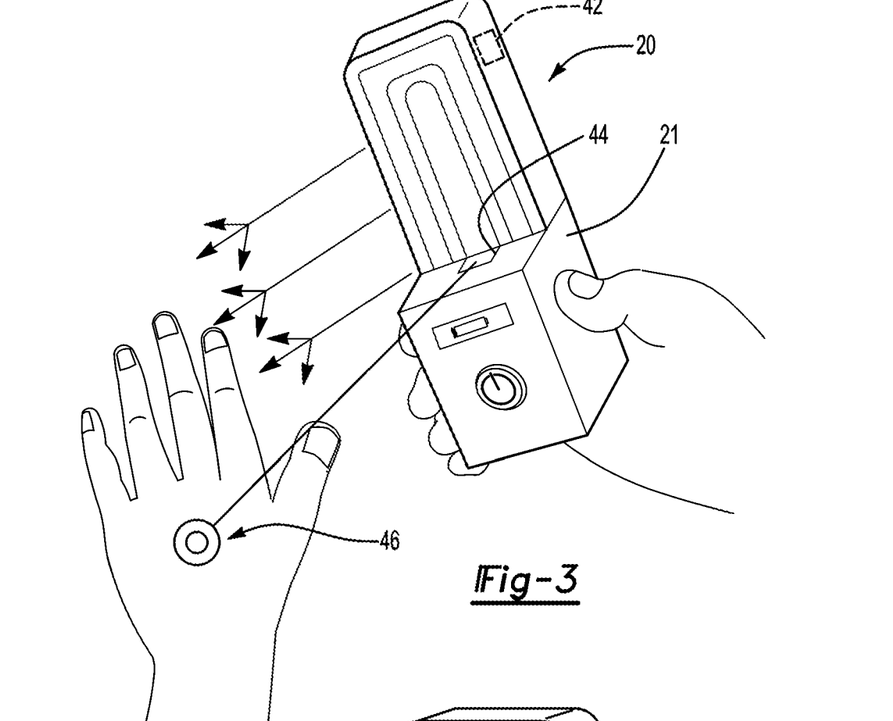
FIG. 3 is a perspective view of the portable device of FIGS. 2A and 2B emitting UVC light and irradiating a human hand.
Figure 4:
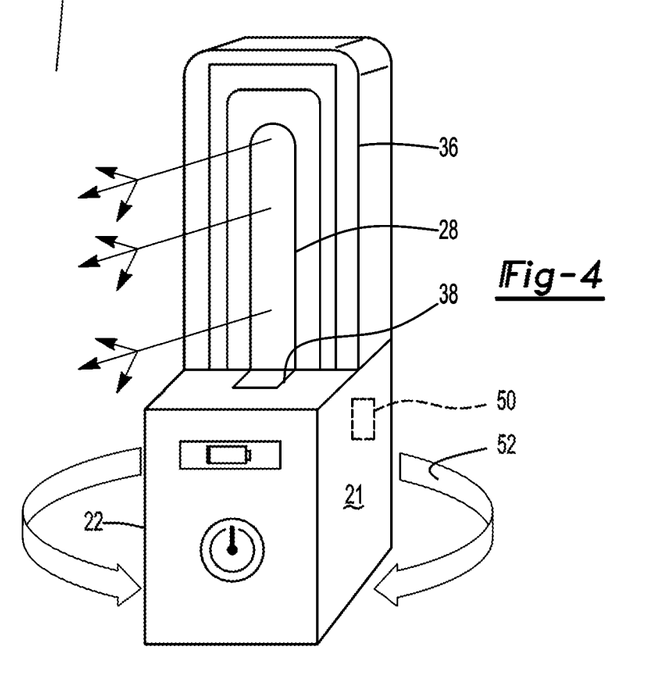
FIG. 4 is a perspective view of the portable device of FIGS. 2A and 2B with a rotatable base to adjust a width of emitted UVC light in accordance with the present invention.
Figure 5A:
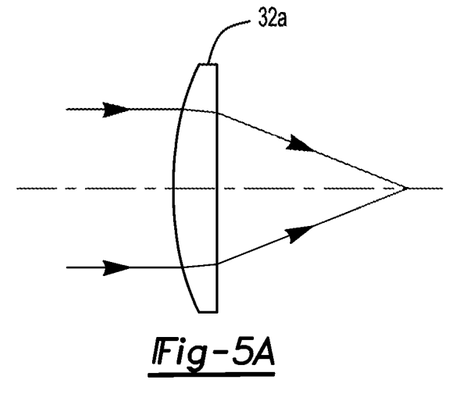
FIGS. 5A-5F are plan views of various lenses for use with the portable device in accordance with the present invention.
Figure 5B:
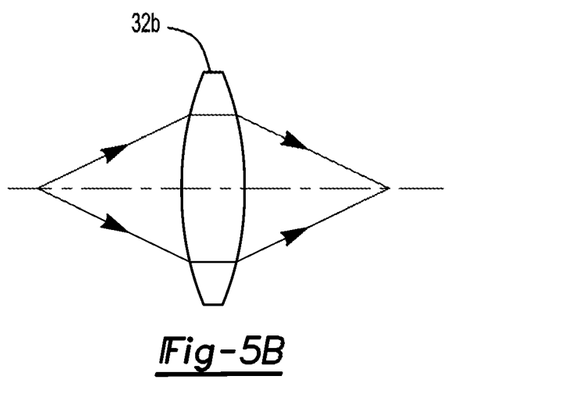
Figure 5C:
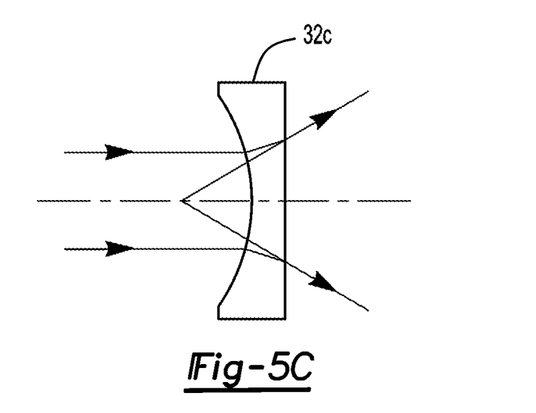
Figure 5D:
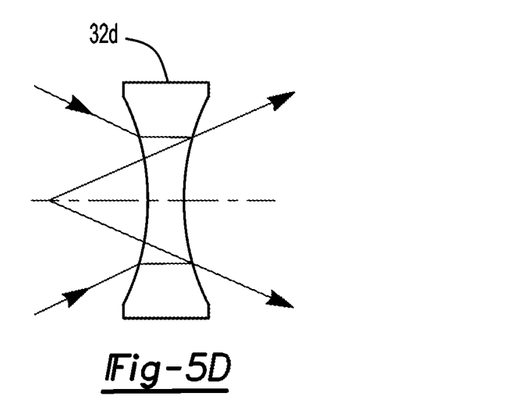
Figure 5E:
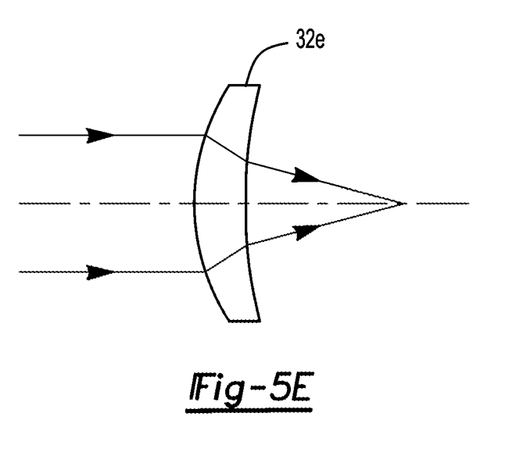
Figure 5F:
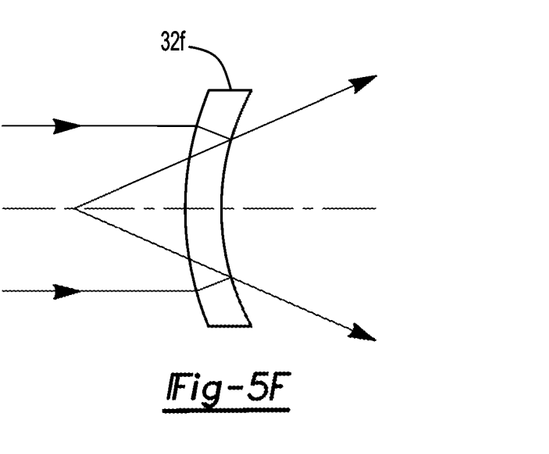

Referring now to FIGS. 3 and 4, the device 20 emits UVC light to irradiate a target object or area to be cleansed. For example, as shown in FIG. 3, a user may hold the device 20 in one hand while irradiating his or her other hand to cleanse the hand of pathogens. The device 20 may include a grip or handle 21 for gripping the device by the user of the device (e.g., holding the device in the user's hand). For example, the device 20 may include a rubberized surface for the user to grip while directing illumination or light toward the surface or air to be sanitized.

The grip or handle 21 may take any shape or form to facilitate the user holding and/or aiming the device 20. In some examples, the handle 21 may be detachable or removable from the device 20 for storage or for cleaning of the handle itself. For example, the handle may screw or clip or snap into place at internal structure of the device 20. The handle portion (the exterior part of the device) thus may be removed from the structure. After removal, the handle 21 may be sanitized by the device 20 or cleaned via another method (e.g., a cleaning fluid) separately. In some examples, the handle 21 may be disposable or otherwise replaceable and replaced periodically. In addition, and as discussed below, other components of the device may be removed and cleaned or serviced or replaced.

The device 20 may have an optimal operating distance. That is, the device 20 may operate most efficiently when disposed a predetermined distance from the epidermis, object or area. For example, the device 20 may preferably operate six to eighteen inches from the object or area. The optimal distance may be around twelve inches. The device 20 includes a visible light emitter 44 that may emit a visible indicia 46 to indicate when the device is at the optimal distance from the epidermis, object or area. For example, when the visible light emitter 44 of the device emits visible crosshairs, as previously discussed, the crosshairs may be fuzzy and out of focus when the device 20 is closer or further than the optimal distance, and the crosshairs may be in focus when the device 20 is at the optimal distance. Instead of crosshairs, any other shape or design may be emitted by the device 20. For example, a single shape or indicia (such as a circle or a polygon such as a square or a triangle, etc.) or a plurality of concentric shapes (e.g., circles or polygons) may be provided to show the field or area that the light is cleaning. The device 20 may indicate the appropriate distance in other ways (e.g., an LED on the device 20 or an audible tone). The device 20 may measure the distance via another sensor (e.g., an infrared distance sensor).

Because the emitted UV light is typically not visible to human eyes, the device 20 may emit other visible light. For example, the device 20 may emit visible light that illuminates approximately the same area as the emitted UV light to provide a visual indication of the area being sanitized. The visible light may be any color (e.g., white, green, red, etc.). The device may emit a visible outline that approximately encompasses the area irradiated by the emitted UV light. For example, a single circle or a plurality of concentric circles may be provided (such as at a lens or mask through which the UV and visible light is emitted) to show the field or area that the light is cleaning, with the visible light emitted at that area. Thus, for example, if the device is close enough to the surface to be cleaned such that the visible light is within one or more of the circles (or any other emitted shape or polygon or indicia) and not outside of that circle or other shape or polygon or indicia, the user may know that the light intensity at the surface is sufficient to clean the surface, but if the visible light is outside of one or more of the circles or other shapes or polygons or indicia, the user may know that the device is too far from the surface so that the light intensity at the surface is not sufficient to clean the surface.

As shown in FIG. 4, the device 20 may emit UVC light in a narrow wavelength band (e.g., at or near 222 nm). The reflective panel 36 disposed behind the lamp 28 may increase the light density in front of the lamp 28, thereby increasing the effective distance between the device 20 and the intended target area. The device 20 may include a refractor to focus the light by, for example, opening or closing an aperture or by moving or manipulating the lens or the reflective panel. The light may be focused, for example, by twisting the base 22 of the device 20, much like twisting an adjustable brass hose nozzle. The light may be focused in any other suitable manner (e.g., pushing a button, sliding a slider, pushing or pulling the base, turning a knob, the lens, or the lamp, etc.). Such adjustment allows for the device 20 to irradiate a broader or narrower swath of area as desired by the user.

Referring now to FIGS. 5A-5F, the device 20 may include a lens of various different configurations in order to adjust the irradiation shape, range, and/or strength. Generally, distance from the sanitation target is inversely proportional to the irradiance at the surface and the distance is proportional to irradiation area. That is, generally, the further the device 20 is away from the target object or surface, the greater the irradiation area, but the weaker the irradiance at the surface. Different lens configurations may modify or optimize these generalities.

For example, a plano-convex lens 32a (FIG. 5A) may be used when the conjugate ratio (i.e., the ratio of the target object/surface distance from the lens over the distance from the lens to the light source) is greater than 5 (i.e., the target object/surface is far away). The plano-convex lens 32a may be shaped cylindrically to generate surface illumination or radiation in the shape of a line. This provides a high density of UV energy in the shape of a line on, for example, a surface that allows the user to sweep the line across the surface rather than holding it in place for an extended period. That is, all of the energy of the emitted UV light may be concentrated into the line, which may greatly reduce the exposure time necessary to sanitize a surface or object. In another example, a bi-convex lens 32b (FIG. 5B) may be used when the typical conjugate ratio is between 0.2 and 5. In yet another example, a plano-concave lens 32c (FIG. 5C) may be used when the ratio is smaller than 0.2 (i.e., the target object/surface is near). A bi-concave lens 32d (FIG. 5D) has a negative focal length and may be used to increase the divergence of the emitted light. In still yet other examples, a positive meniscus lens 32e (FIG. 5E) or a negative meniscus lens 32f (FIG. 5F) may be used alone or with other lenses to create a compound lens assembly. The positive meniscus lens may shorten the focal length and increase numerical aperture without introducing significant spherical aberration, while the negative meniscus lens may increase the focal length and decrease the numerical aperture.

The device 20 may include a single lens or multiple lens that are used in combination to form a compound lens. The device 20 may enable the user to switch between different lenses based on the intended use. For example, the lens may be modular and swappable with other lenses. The device 20 may include multiple lenses that the user may switch between (e.g., by rotating a wheel of lenses or using some other lens selector 48). The device 20 may emit collimated or non-collimated light. The device 20 may use a lens that limits light absorption or reflection of emitted UV light. For example, the lens may be an uncoated UV fused silica lens.

Referring again to FIG. 3, the device, or more specifically, the lamp 28, may be positioned at or within approximately 12 cm from a human appendage or surface being disinfected. Notably, locating the lamp 28 approximately 12 cm away from the human appendage causes no adverse effect to the human appendage while eradicating pathogens. In one embodiment, the lamp 28 is slowly scanned while emitting far-UVC light to irradiate the surface or appendage subject to allow sufficient irradiation time to destroy the pathogens. It should be understood that the optics (e.g., a lens) may provide substantive alterations in time and intensity of the far-UVC irradiation. In a further embodiment, the lamp 28 is positioned at or within about 6 cm from the human appendage or surface being disinfected while the lamp 28 is slowly scanned over the human appendage or surface. In a still further embodiment, the lamp 28 is positioned at or within about 3 cm from the human appendage or surface being disinfected while the lamp 28 is slowly scanned over the human appendage or surface. Distance, lamp irradiating energy and optics all may contribute to the amount of time required to sufficiently eliminate pathogens disposed upon an epidermis of a human appendage, surface, and even air within the irradiation area.

Optionally, the device 20 may comprise a modular design that allows for easy replacement of a variety of parts. For example, a handle, a light source (both visible and non-visible) a filter, and/or a lens of the device 20 may be removable and replaceable by a user of the device 20 without replacing the entire device 20. The handle or housing may be removed, and/or the light source may be removed and replaced and/or the power source or battery may be removed and replaced and/or the filter or lens may be removed and replaced. The various components may snap or otherwise attach to a central circuit element or device or structure (including a printed circuit board and control circuitry for operating and controlling the device).

Therefore, in accordance with the present invention, the device provides a means to sanitize small surface areas and/or the air surrounding the surface areas. For example, shoes before entering house, faucets in restroom, door handles, public table before eating, utensils, toys, remote control, sinks, office spaces, etc. When activated, the device works to eliminate harmful, illness causing bacteria and germs that are not visible to the human eye.

Changes and modifications in the specifically described embodiments can be carried out without departing from the principles of the invention, which is intended to be limited only by the scope of the appended claims, as interpreted according to the principles of patent law including the doctrine of equivalents.

The invention claimed is:

1. A handheld UVC device for generating and emitting UVC light on selected surfaces, localized areas and air surrounding a surface, the handheld UVC device comprising:
an irradiation portion, wherein the irradiation portion, when powered, provides light in the UVC spectrum for generating and emitting UVC light toward a surface;
an activation portion, wherein the activation portion provides selective activation of the irradiation portion for a time duration sufficient to episodically generate and emit UVC light to sanitize the surface;
a visible light emitter, wherein the visible light emitter, when powered, emits visible indicia to indicate an area of the surface that is irradiated by the UVC light, wherein the visible indicia is in focus when the handheld UVC device is disposed at an optimal distance from the surface to be sanitized, and wherein the visible indicia is not in focus when the irradiation portion of the handheld UVC device is not disposed at the optimal distance from the surface to be sanitized; and
a grip, wherein the grip provides a gripping surface for a user to grip and hold the handheld UVC device and direct the irradiation portion toward the surface to be sanitized and to emit UVC light toward the surface to be sanitized.

2. The handheld UVC device of claim 1, wherein the grip is detachably attached to the handheld UVC device.

3. The handheld UVC device of claim 1, comprising at least one lens, wherein the UVC light passes through the at least one lens to focus or disperse the UVC light.

4. The handheld UVC device of claim 3, wherein the at least one lens comprises at least one selected from the group consisting of (i) a piano-convex lens, (ii) a bi-convex lens, (iii) a piano-concave lens, (iv) a bi-concave lens, (v) a positive meniscus lens, and (vi) a negative meniscus lens.

5. The handheld UVC device of claim 1, wherein the irradiated portion is detachably attached to the handheld UVC device.

6. The handheld UVC device of claim 1, wherein the visible indicia indicates when a distance from the irradiation portion of the handheld UVC device to the surface to be sanitized is greater than a maximum effective sanitizing distance of the UVC light.

7. The handheld UVC device of claim 1, further comprising a filter configured to attenuate wavelengths of the UVC light below 200 nm and above 235 nm.

8. The handheld UVC device of claim 7, wherein the filter is replaceable.

9. The handheld UVC device of claim 8, wherein the replaceable filter comprises a removable filter cartridge.

10. The handheld UVC device of claim 2, wherein the detachably attached grip is configured to be sanitized by the handheld UVC device when detached.

11. The handheld UVC device of claim 1, comprising a piano-convex lens, wherein the piano-convex lens is configured to focus the UVC light into a line.

12. The handheld UVC device of claim 4, comprising a lens selector configured to select the at least one lens.

13. The handheld UVC device of claim 1, comprising an eye detection sensor, and wherein responsive to the eye detection sensor detecting an eye in the path of the UVC light, the handheld UVC device depowers the irradiation portion.

14. The handheld UVC device of claim 13, wherein the eye detection sensor comprises a camera.

15. The handheld UVC device of claim 1, wherein the irradiation portion, when powered, provides light in the far-UVC spectrum for generating and emitting far-UVC light.

16. The handheld UVC device of claim 1, wherein the emitted visible indicia indicates when the intensity of the emitted UVC light at the surface is sufficient to sanitize the surface.

17. The handheld UVC device of claim 1, wherein the emitted visible indicia indicates when the intensity of the emitted UVC light at the surface is not sufficient to sanitize the surface.

18. The handheld UVC device of claim 1, wherein the visible indicia defines concentric shapes on the selected surfaces.

19. The handheld UVC device of claim 18, wherein the shapes comprise circles.

20. The handheld UVC device of claim 18, wherein the shapes comprise polygons.

* * * * *